United States Patent [19]
Jardon et al.

[11] 4,206,518
[45] Jun. 10, 1980

[54] INTRAOCULAR LENS DEVICE

[76] Inventors: Fritz Jardon, 25050 W. 10-Mile Rd., Southfield, Mich. 75034; Albert D. Ruedemann, Jr., 1018 3-Mile Rd., Grosse Pointe Park, Mich. 48230

[21] Appl. No.: 764,042

[22] Filed: Jan. 31, 1977

[51] Int. Cl.² ............................ A61F 1/16; A61F 1/24
[52] U.S. Cl. ............................................................ 3/13
[58] Field of Search .......................................... 3/13, 1

[56] References Cited

U.S. PATENT DOCUMENTS

| 2,834,023 | 5/1958 | Lieb ........................................ 3/13 X |
| 3,228,741 | 1/1966 | Becker .................................... 3/13 X |
| 3,991,426 | 11/1976 | Flom et al. ................................ 3/13 |
| 3,994,027 | 11/1976 | Jensen et al. ............................. 3/13 |

FOREIGN PATENT DOCUMENTS 2313010 12/1976 France ........................................... 3/13

OTHER PUBLICATIONS

"The Intraocular Implant Lens Development and Results," published by the Williams and Wilkins Co., Baltimore, Md., 1975, pp. 16–23.
"A Weightless Iseikonic Intraocular Lens", by R. D. Binkhorst et al., American Journal of Ophthalmology, vol. 58, No. 1, Jul. 1964, pp. 73–78.
"History of Intraocular Implants", by D. P. Choyce, Annals of Ophthalmology, Oct. 1973, pp. 1113–1120.
"Optical Properties of Buried Corneal Silicone Prostheses", by D. Miller et al., American Journal of Ophthalmology, vol. 66, No. 4, Oct. 1968, pp. 633–640.

Primary Examiner—Ronald L. Frinks
Attorney, Agent, or Firm—Joseph W. Farley

[57] ABSTRACT

An intraocular lens device made of a transparent, flexible, medical grade silicone elastomer molded to form a generally cylindrical lens body implantable within the pupillary margin of the iris and to form a plurality of flexible plate-like attachment tabs which project laterally from the lens body anteriorly, or posteriorly, or both anteriorly and posteriorly of the iris, and which tabs are connectable to the iris by teflon pegs.

14 Claims, 16 Drawing Figures

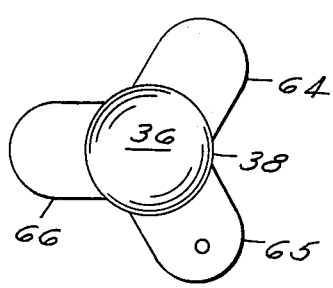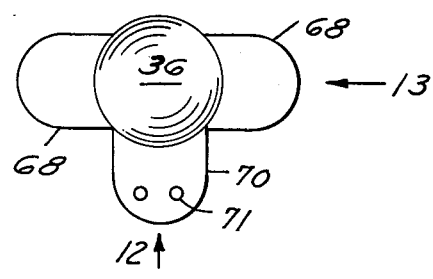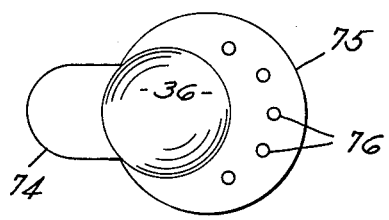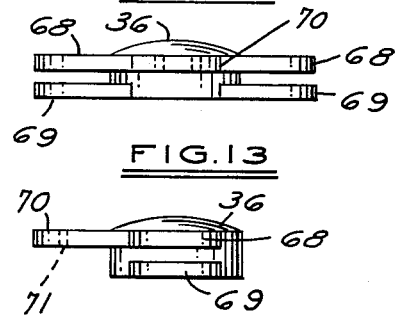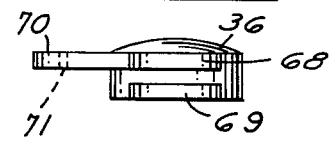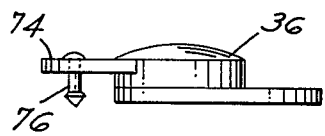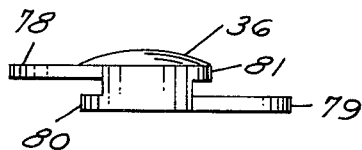

INTRAOCULAR LENS DEVICE

This invention relates to an improved lens device which can be implanted intraocularly when defects occur such as permanent loss of corneal clarity, or loss of clarity of the natural lens due to cataract, and replace intraocular volume when the natural lens is extracted.

Various types of intraocular implant lens devices have been proposed, and surgical procedures for their insertion into the eye have been developed. Examples of such prior devices may be found in U.S. Pats. Nos. 3,866,249, 3,711,870, 3,673,616 and 2,834,023; but, to the best of our knowledge, no intraocular lens implant device has been developed which has a good record of patient tolerance. Some of the problems encountered with such prior devices are discussed in the introductory portion of the above-mentioned U.S. Pat. No. 3,866,249, to which reference is made, and in general, it seems that these problems with prior devices stem from the materials employed in their construction and from the means used for fixing them within the intraocular tissues.

The intraocular lens device of the present invention is made of a transparent, flexible, medical grade, silicone elastomer formed into a generally cylindrical lens body having a desired refractive power and a marginal portion adapted to be fitted within the pupillary margin of the iris; means for the fixation of the lens device to the iris including flexible plate-like tab means comprising flaps formed of the silicone material and projecting outwardly from the marginal portion of the lens body for placement in overlapping relation with at least one of the anterior and posterior surfaces of the iris; and means for attaching said flexible tab means to the iris.

The silicone elastomer provides a material that is inert and has been successfully used in multiple applications around the body; e.g., extraocular, intravascular, intracardiac, etc. When employed with the lens construction of the invention, the result is to provide an intraocular lens device which is reasonably inert, very light in weight, and flexible; and, all of these features minimize the possibility of post-operative complications which experience shows have been primarily due to irritation of the intraocular tissues by the implanted device.

Various arrangements may be employed for the flexible plate-like fixation tabs which may be molded in one piece with the lens body portion of the device or which may be separately attached to the lens body, as desired.

The foregoing and other features and advantages of the invention will appear from the following description of the representative embodiments thereof shown in the accompanying drawings.

DESCRIPTION OF THE DRAWINGS

FIG. 10 is a plan view of another alternate form of lens device of the invention;

FIG. 11 is a plan view of a further alternate construction of the lens device of the invention;

FIG. 12 is a side elevation of the device of FIG. 11, taken in the direction of the arrow 12;

FIG. 13 is a side elevation of the device of FIG. 11, taken in the direction of the arrow 13;

FIG. 14 is a plan view of another alternate construction of the lens device of the invention;

FIG. 15 is a side elevation of the device of FIG. 14; and,

FIG. 16 is a side elevation of a further alternate construction.

DESCRIPTION OF THE PREFERRED EMBODIMENTS

Figure 1:
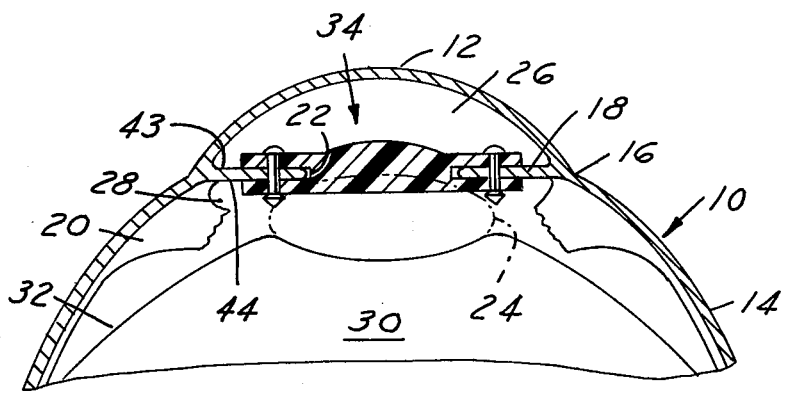
FIG. 1 is a sectional elevation of the human eye with an intraocular lens device of the invention implanted therein.

FIG. 1 illustrates, somewhat schematically, the major components of the outer portion of an eyeball or globe 10. These portions include the cornea 12, the sclera 14, the limbus 16 and the iris 18 which extends from the ciliary body 20 and which includes the circular pupillary margin 22. A natural lens 24 is indicated in broken line and is normally attached to the ciliary body 20. The iris 22 and the natural lens 24 normally divide the interior of the eye into an anterior chamber 26 filled with aqueous humor and a posterior chamber 28 filled with the vitreous body 30 covered by the hyaloid membrane 32.

Figure 2:
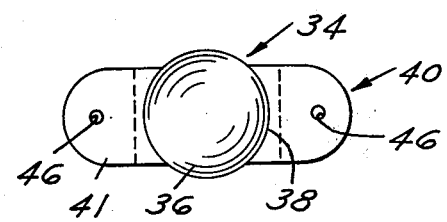
FIG. 2 is a plan view of one form of lens device of the invention.
Figure 3:
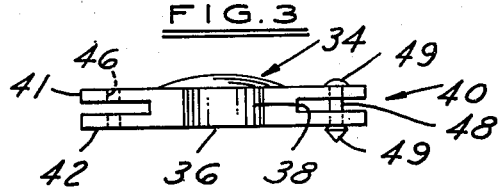
FIG. 3 is a side elevation of the device shown in FIG. 2.

The natural lens 24 of the eye 10 has been removed and replaced by an intraocular lens device 34 constructed in accordance with the present invention and shown in FIGS. 2 and 3. A generally cylindrical lens body 36 is formed with a desired refractive power and includes a cylindrical marginal portion 38 adapted to be fitted within the pupillary margin 22 of the iris 18. Both the anterior and posterior surfaces of the lens body 36 can be used to provide the optical power desired. Means 40 for the fixation of the device 34 to the iris 18 include pairs of anterior and posterior flexible tabs 41 and 42 which project outwardly from the marginal portion 38 of the lens body 36 and are adapted to be placed, respectively, in overlapping relation with the anterior and posterior surfaces 43 and 44 of the iris 18. Aligned apertures 46 are formed in each pair of tabs 41 and 42, and a headed peg 48 is adapted to be inserted through the apertures 46 and through the iris tissue, thereby attaching the flexible tabs to the iris.

The lens body 36 and the tabs 41 and 42 are made from a silicone elastomer, preferably one of medical grade which can be sterilized. This material is light in weight, is transparent, is flexible, and is inert, being non-irritating and not affected by body fluids. This material also preferably has a refractive index slightly higher than the aqueous humor of the eye.

A molding technique is preferably used for forming the lens body 36, and the molding process may also include the formation of the tabs 41 and 42, although a corresponding tab of each pair may be formed separately and then bonded to the lens body 36 in order to reduce the expense of the mold. Molding is carried out by mixing the silicone elastomer materials, evacuating the mixture to remove any air bubbles entrapped therein, placing the evacuated material in a mold, again evacuating to remove any air bubbles, and finally curing.

For human use, the overall length dimension of the device 34, including the length of the tabs 41 and 42 on each side of the lens body 36, would not normally exceed ten millimeters—as an example, the lens body 36 may have a diameter of four millimeters and each pair of the tabs 41 and 42 a maximum lateral projection of two and one-half millimeters giving an overall length of nine millimeters for the device. The thickness of each of the tabs 41 and 42 is a fraction of a millimeter, making the tabs very flexible.

The attachment pegs 48 are preferably made of Teflon, and each peg is provided at its ends with enlarged heads 49 which can be pressed through the apertures 46 in the tabs 41 and 42 into interlocking engagement therewith, as shown in FIG. 3.

The alternate forms of construction of the device, illustrated in FIGS. 4–10, differ from the lens device 34 described above principally in the construction and arrangement of the flexible fixation tabs.

Figure 4:
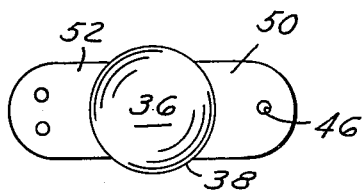
FIG. 4 is a plan view of an alternate form of the lens device of the invention.
Figure 5:
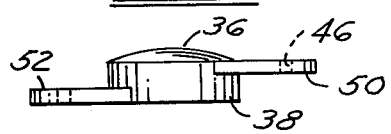
FIG. 5 is a side elevation of the device shown in FIG. 4.
Figure 6:
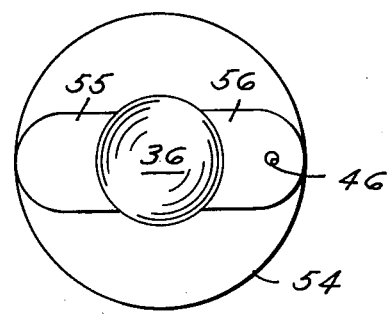
FIG. 6 is a plan view illustrating another form of lens device of the invention.
Figure 8:
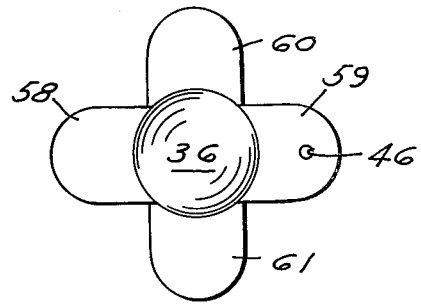
FIG. 8 is a plan view of a further form of lens device of the invention.
Figure 7:
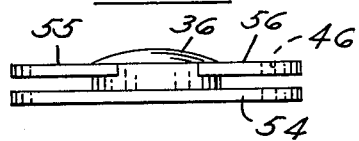
FIG. 7 is a side elevation of the device shown in FIG. 6.
Figure 9:
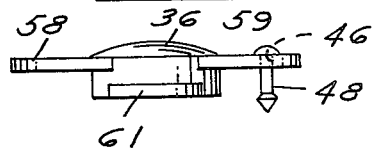
FIG. 9 is a side elevation of the device shown in FIG. 8.

In FIGS. 4 and 5, the lens body 36 is provided with an anterior fixation tab 50 projecting to one side of the marginal portion 38, and with a diametrically opposed posterior fixation tab 52. The lens body 36 in FIGS. 6 and 7 is provided with a posterior circular flexible fixation disk 54 and with diametrically opposed anterior fixation tabs 55 and 56. In FIGS. 8 and 9, the lens body 36 has diametrically opposed anterior fixation tabs 58 and 59 and diametrically opposed posterior fixation tabs 60 and 61 which are arranged in right angular relation to the anterior tabs 58 and 59. A group of three fixation tabs 64, 65 and 66, arranged in circumferentially spaced relation around the marginal portion 38 of the lens body 36, is shown in FIG. 10, and ordinarily these tabs 64–66 would all be either anteriorly or posteriorly placed.

Other alternate constructions appear in FIGS. 11–16. In FIGS. 11–13, two pairs of anterior and posterior tabs 68 and 69 project from the lens body 36 in diametrically opposed relation, and an anterior tab 70 is disposed circumferentially between the anterior tabs 68. The tab 70 is provided with a pair of holes 71 which receive a suture for attaching the lens device to the iris. FIGS. 14 and 15 show a lens body 36 having an anterior tab 74 projecting from one side, and a generally circular posterior disc 75 arranged in eccentric relation to the axis of the lens body so as to project to the opposite side in varying amounts. A series of suture receiving holes 76 in the disc 75 and a peg 76 in the tab 74 are provided for attachment of the lens device. The construction of FIG. 16 has an anterior tab 78 and a diametrically opposite posterior tab 79 which cooperate, respectively with a posterior ledge 80 and an anterior ledge 81 for holding the device within the pupillary margin, supplemented by a suture or a peg attachment, as desired. The examples illustrated and described herein demonstrate the versatility of the invention as far as the fixation of the lens device is concerned. The particular form of fixation means employed can be varied in order to meet the requirements of a particular patient. Also, the suture form of attachment illustrated in the lens devices of FIGS. 11 and 14 can be employed in place of the peg form of attachment illustrated in other modifications of the lens devices, particularly those lens devices which do not have an opposed pair of anterior and posterior tabs.

The surgical procedure used in the implantation of an intraocular lens device of the invention is straightforward. The eye is prepped and draped in the usual manner. A standard lid speculum is placed and a superior rectus suture is placed at 12:00. A flap may or may not be utilized. A limbal incision is placed with standard instrumentation using knife or blade and enlarged from 10:00 to 2:00 position. A peripheral iridectomy is performed at the 12:00 position extending in a triangular fashion with the apex inferior. The natural lens 24 is then extracted either extracapsularly (or intracapsularly), removing the nucleous into the anterior chamber and extracting it and then washing out the bulk of the cortical material leaving peripheral cortical remnants and capsule; or if an intracapsular extraction is performed, it is wise to have the hyaloid face as posteriorly placed as possible. The same procedure should be used in an intraocular operation in which the lens is removed in toto. The intraocular lens device 34 is then inserted into the anterior chamber 26, directing one of the posterior tabs 42 beneath the iris at 6:00. Then, by pulling the iris superiorly, the anterior fixation tab 41 is placed over the iris. A small smooth tipped forceps is used to insert the peg 48 through the apertures of the superiorly placed pair of tabs 41 and 42, attaching these tabs together into the iris iredectomy opening. The iris is then dressed and allowed to contract around the marginal portion 38 of the lens body 36. The wound is then closed tightly and the anterior chamber 26 may be filled with air or saline ointment. Pilocarpine is placed in the anterior chamber 26 or on the cornea 12 and a patch is put on the eye. It is important that the anterior chamber 26 be maintained from the point of operation therefrom. Local miotic and anti-inflammatory drops should be utilized routinely in the post-operative period and for a reasonable post-operative period. Systemic antibiotics should be used.

The power of the lens to be used for a patent can be computed using standard technique and ultrasound devices to determine the axial length of the eye. Also, a lens for human use should preferably incorporate an ultraviolet filter, added as a coating to the lens body 36.

What is claimed is:

1. An intraocular lens device for implantation in the eye and comprising a lens body formed from a medical grade silicone elastomer having a refractive index slightly higher than the aqueous humor of the eye and a desired refractive power, said lens body including a generally cylindrical marginal portion adapted to be fitted within the pupillary margin of the iris;

and means for the fixation of the lens device to the iris, said fixation means including a plurality of flexible plate-like tabs formed of said silicone material and projecting outwardly from said marginal portion of the lens body for placement in overlapping relation with at least one of the anterior and posterior surfaces of the iris.

2. An intraocular lens device according to claim 1 wherein the thickness of said flexible tabs is less than one millimeter.

3. An intraocular lens device according to claim 1 wherein said fixation means includes a circular disk for placement in overlapping relation with the posterior surface of the iris.

4. An intraocular lens device according to claim 3 wherein said circular disk is arranged in eccentric relation to the axis of said lens body.

5. An intraocular lens device according to claim 3 wherein said fixation means includes a pair of tabs for placement in overlapping relation with the anterior surface of the iris on opposite sides of the pupillary margin.

6. An intraocular lens device according to claim 5 further including apertures formed in said disk and pairs of tabs, and attachment means insertable through said apertures.

7. An intraocular lens device according to claim 1 wherein said fixation means further comprises an aperture extending through at least one of said tabs at a location radially outward from said marginal portion of the lens body.

8. An intraocular lens device according to claim 7 further comprising an attachment member having headed ends each larger than said aperture, one of said headed ends being pressable through said aperture.

9. An intraocular lens device according to claim 1 wherein at least one of said tabs is displaced in a direction axially of the lens body from another of the tabs, said one tab being placeable in overlapping relation with one of said anterior and posterior surfaces of the iris while another of the tabs is placeable in overlapping relation with the other of said surfaces.

10. An intraocular lens device according to claim 1 wherein said fixation means includes a plurality of pairs of tabs, one tab of each pair being spaced from the other tab of each pair in a direction axial of the lens body for placement of a pair of tabs in overlapping relation with opposed portions of the anterior and posterior surfaces of the iris.

11. An intraocular lens device according to claim 10 wherein said fixation means further includes a single tab placeable in overlapping relation with the anterior surface of the iris, and at least one suture receiving aperture formed in said single tab.

12. An intraocular lens device according to claim 10 further including aligned apertures in at least one pair of tabs, and an attachment member insertable through said apertures.

13. An intraocular lens device according to claim 12 wherein said attachment member is provided with headed end portions for interlocking engagement with said one pair of tabs.

14. An intraocular lens device according to claim 1 wherein said fixation means includes a tab projecting from said marginal portion of the lens body a certain distance for placement in overlapping relation with one of the anterior and posterior surfaces of the iris and a ledge spaced axially of said marginal portion of the lens body from said tab and projecting outwardly from said portion a distance less then said certain distance for placement in overlapping relation with the other of said surfaces of the iris.

* * * * *